United States Patent [19]

Fehling et al.

[11] Patent Number: 4,977,900
[45] Date of Patent: Dec. 18, 1990

[54] MICROSURGICAL FORCEPS WITH CLEANING FLUID PASSAGE

[76] Inventors: Guido Fehling, Frankenstrasse 21, 8757 Karlstein; Gunter Stoffel, Kantstrasse 35, 7204 Wurmlingen, both of Fed. Rep. of Germany

[21] Appl. No.: 287,223

[22] Filed: Dec. 21, 1988

[30] Foreign Application Priority Data

Jan. 8, 1988 [DE] Fed. Rep. of Germany ....... 3800331

[51] Int. Cl.⁵ .............................................. A61B 10/00
[52] U.S. Cl. ....................................... 128/751; 600/22
[58] Field of Search ....................... 128/321, 749, 751; 604/22; 606/83, 205, 207, 167, 170, 168

[56] References Cited

U.S. PATENT DOCUMENTS

| | | | |
|---|---|---|---|
| 2,790,437 | 4/1957 | Moore | 128/321 |
| 3,964,468 | 6/1976 | Schulz | 128/321 |
| 4,522,206 | 6/1985 | Whipple et al. | 604/22 |
| 4,569,131 | 2/1986 | Falk et al. | 128/751 |
| 4,646,751 | 3/1987 | Maslanka | 128/751 |
| 4,763,668 | 8/1988 | Macek | 128/751 |

FOREIGN PATENT DOCUMENTS 1266446  4/1968  Fed. Rep. of Germany ........ 606/22

Primary Examiner—C. Fred Rosenbaum
Assistant Examiner—William Lewis
Attorney, Agent, or Firm—Mason, Fenwick & Lawrence

[57] ABSTRACT

A microsurgical forceps, particularly for biopsy, comprises a tube, a shaft therein connected to a hollow rod which is coaxial therewith and is axially displaceable by one of a pair of pivotally connected handles. A fluid cleaning agent can be conducted under pressure through the rod end into a space between the tube and shaft to flush the forceps.

8 Claims, 2 Drawing Sheets

MICROSURGICAL FORCEPS WITH CLEANING FLUID PASSAGE

BACKGROUND OF THE INVENTION

The invention relates to a microsurgical biopsy forceps, with provision for axially introducing a cleaning liquid into it.

Microsurgical Forceps are used as biopsy forceps to remove intracorporeal tissue samples. These reusable forceps, more economical than disposable forceps, can be flushed with a preferably liquid cleaning agent to clean them. The cleaning agent is conducted into the handle part under pressure, flushing the shape of the forceps from the proximal end to the distal end.

It is known that a fluid inlet connection, for example a so-called Luer-Lock connection, can be provided on the handle of a forceps radially perpendicular to the forceps longitudinal axis, for supplying cleaning agent see, for example, Maslanka U.S. Pat. No. 4,646,751.

This connection, however, makes the forceps instrument costly to manufacture and may interfere with the handling and manipulation of the forceps by the user and may impede the viewing of the relevant part of the patient by the user.

Objects of the invention are to provide a microsurgical forceps which is simple in construction and which permits reliable cleaning without impeding manipulation or viewing by the user.

SUMMARY OF THE INVENTION

In the microsurgical forceps according to the present invention, a flexible axially displaceable shaft within a flexible tube of the forceps has a rod mounted on its proximal end, the rod having a coaxial bore to conduct fluid cleaning agent. The coaxial feed of the fluid cleaning agent at the proximal end of the forceps instrument does not interfere with the manipulation of the instrument and viewing of the operational site by the user. Feed through the tubular shaft i simple in construction and requires no additional connecting elements. The hollow rod transmits axial motion from the handle to the flexible actuating shaft. The rod, which is guided so that it is displaceable only axially, is hermetically sealed against pressure by a simple construction.

The forceps handle includes a holow cylindrical handle sleeve coaxially therein, the chamber therein being closed by a coupling nut. An annular seal is located axially in the handle chamber and surrounds the rod.

The invention is described hereinbelow in greater detail with reference to a preferred embodiment shown in the drawing.

DESCRIPTION OF THE PREFERRED EMBODIMENT

The microsurgical forceps preferably constructed as biopsy forceps, which have pincers or jaws connected to the distal ends of a tube and a shaft reciprocable therein, further comprises a scissor-like handle of known construction having, a fixed shank 10 and a second shank 11 pivotably connected thereto. Both shanks are provided with loops for the user's fingers.

Figure 2:
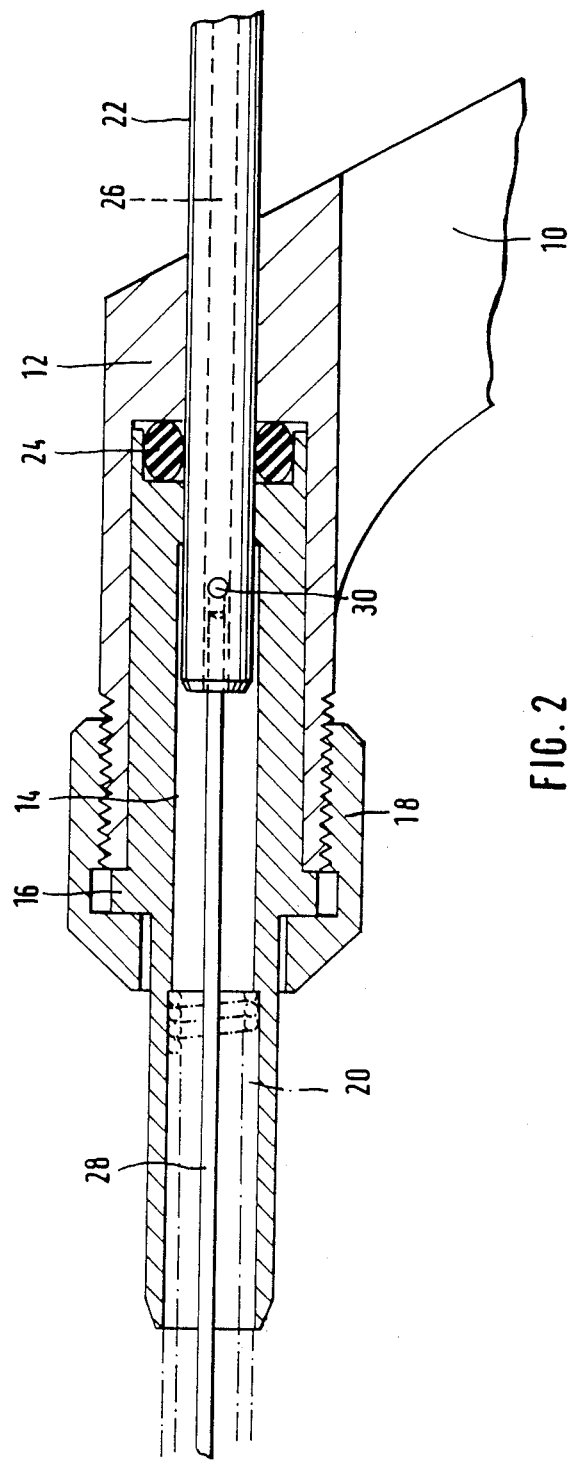
FIG. 2 is a partial axial section of the forceps instrument.

A handle part 12 is formed integrally with and at an angle to shank 10, at the end of fixed shank 10 opposite the loop. Handle part 12, as shown in FIG. 2, has a coaxial blind hole at its distal end, into which hole a hollow cylindrical handle sleeve 14 fits. Handle sleeve 14 has an external bead 16 abutting the distal end face of handle part 12 and is held in handle part 12 by a coupling nut 18, which surrounds bead 16 of handle chamber sleeve 14 and is threaded onto an external thread of handle part 12.

A forceps tube 20 is sealed into the distal end of handle sleeve 14 which extends through nut 18, the tube being a flexible spiral wire in the embodiment shown.

A hollow rod 22 with an annular cross section is guided coaxially with handle chamber sleeve 14 through the proximal end of handle part 12 and into handle chamber sleeve 14. Rod 22 is axially displaceable. An annular seal 24, preferably in the form of an O-ring, hermetically seals the passage of rod 22 into handle chamber sleeve 14. the annular seal 24 is located axially between the proximal inner end face of handle chamber sleeve 14 and the end of a blind hole in handle part 12 and is compressed axially force by the axial pressure of nut 18 so that is radially abuts the outer circumference of rod 22 in sealing fashion. A cylindrical projection on the outer circumference of handle chamber sleeve 14 abuts the outer circumference of annular seal 24.

Rod 22 is traversed by a coaxial bore 26 serving to conduct the fluid cleaning agent into handle chamber sleeve 14 and forceps tube 20. The proximal end 23 of rod 22 is connected directly to a source of high-pressure cleaning fluid.

A solid actuating shaft 28 is incorporated coaxially into forceps tube 20 and has a diameter smaller than the inside diameter of bore 26 of rod 22. The proximal end of actuating shaft 28 fits coaxially into bore 26 and is fastened to rod 22 by a T-shaped connector 30. Since the diameters of actuating shaft 28 and of T-shaped connector 30, and especially of the crosspin of this connector, are smaller than the inside diameter of bore 26, there is a sufficient space cross section in bore 26, even at the distal end of rod 22, to allow passage of the fluid cleaning agent.

Figure 1:
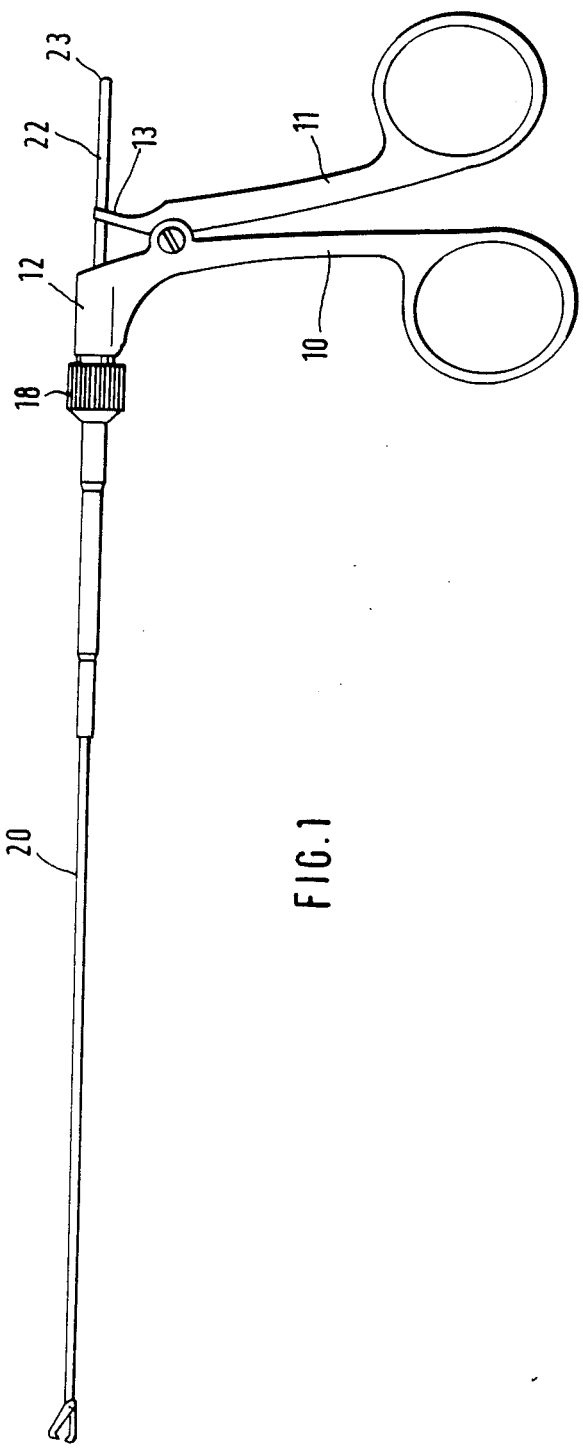
FIG. 1 is a general view of a forceps instrument according to the invention.

Pivotable shank 11 of the handle, see FIG. 1, has a fork 13 at the end opposite loop for the user's finger by means of which it engages a circumferential groove on rod 22. In this fashion, rod 22 and hence actuating shaft 28 can be displaced axially by means of the handle to actuate the forceps, since actuating shaft 28 extends within and along the entire length of tube 20.

What is claimed is:

1. Microsurgical forceps comprising first and second pincer jaws connected to a tube and to a shaft reciprocable in said tube:

first and second hand engageable elements connected for relative movement,
   said tube extending from one said element and connected to said first jaw,
   means for securing said tube to said first element,
   said shaft being in said tube and of lesser diameter than the internal diameter of said tube to provide a space therebetween, said shaft connected to said second jaw and having a proximal end in said one element, and
   means for connecting said shaft to said second element for movement therewith, comprising a hollow rod having a distal end, and means for connecting said hollow rod distal end to the proximal end of said shaft substantially coaxially therewith and for providing a fluid connection between the hollow of said rod and said space between said shaft and said tube, whereby a fluid cleaning agent may be introduced into said space through said hollow rod.

2. Microsurgical forceps are set forth in claim 1, said shaft having a smaller diameter than the hollow of said hollow rod, and said connecting means comprising a T-shaped connector.

3. Microsurgical forceps as set forth in claim 1, said first element having:
- a handle part at an angle thereto,
- a blind hole in said handle part and coaxial therewith,
- a hollow cylindrical handle chamber sleeve in said blind hole,
- the distal end of said rod extending into said sleeve, and
- sealing means carried by said handle chamber sleeve for sealingly engaging the exterior of said rod.

4. Microsurgical forceps as set forth in claim 3, and means comprising a connecting nut threadedly engaging said handle part for holding said handle chamber sleeve in said blind hole of said handle part.

5. Microsurgical forceps as set forth in claim 3, said means for securing said tube comprising the proximal end of said tube sealed in said handle chamber sleeve.

6. Microsurgical forceps as set forth in claim 1, said means for connecting said shaft to said other element comprising a groove in said rod and a forked end on said other element engaged in said groove.

7. A microsurgical instrument comprising first and second jaws,
- a tube having a proximal end and a distal end and said first jaw connected to the distal end thereof,
- a shaft having a proximal end, and a distal end connected to the second jaw, said shaft being in said tube along substantially the entire length of said tube, and of lesser diameter than the internal diameter of said tube,
- means for conducting fluid from the proximal end of said tube to the distal end of said tube comprising a space between said tube and said shaft extending from the proximal end to the distal end of said tube,
- means for axially moving said shaft in said tube comprising a hollow link axially of and connected to the proximal end of said shaft, and a handle connected to said hollow link for axially moving said hollow link and said shaft, and
- means for fluid connecting said hollow link and said space between said tube and said shaft at the proximal end of said tube,
- whereby fluid may be conducted through said hollow link and into said space.

8. In a microsurgical instrument as set forth in claim 7, said instrument comprising a second handle, said tube secured to said second handle, said fluid connecting means comprising a chamber in said second handle, portions of said shaft and link being in said chamber.

* * * * *